US005698677A

United States Patent [19]
Eibl et al.

[11] Patent Number: 5,698,677
[45] Date of Patent: Dec. 16, 1997

[54] STABLE PREPARATION FOR THE TREATMENT OF BLOOD COAGULATION DISORDERS

[75] Inventors: Johann Eibl; Hans Peter Schwarz; Jürgen Siekmann; Peter Turecek, all of Vienna, Austria

[73] Assignee: Immuno Aktiengesellschaft, Vienna, Austria

[21] Appl. No.: 435,128

[22] Filed: May 5, 1995

[30] Foreign Application Priority Data

May 6, 1994 [DE] Germany .................. 44 16 166.2

[51] Int. Cl.⁶ .................................................. A61K 35/14
[52] U.S. Cl. .................. 530/381; 530/380; 530/382; 530/383; 530/384; 424/450; 424/529; 435/236
[58] Field of Search .................. 435/236; 424/450, 424/529; 530/350, 380, 382, 383, 384, 381

[56] References Cited

U.S. PATENT DOCUMENTS

| 4,241,046 | 12/1980 | Papahadjopoulos et al. | 424/19 |
|---|---|---|---|
| 4,348,384 | 9/1982 | Horikoshi et al. | 424/101 |
| 4,610,880 | 9/1986 | Giles et al. | 424/101 |
| 4,640,834 | 2/1987 | Eibl et al. | 424/94 |
| 4,721,618 | 1/1988 | Giles et al. | 424/101 |
| 4,937,324 | 6/1990 | Fujikawa et al. | 530/397 |
| 5,198,349 | 3/1993 | Kaufman | 435/69.6 |
| 5,225,537 | 7/1993 | Foster | 530/380 |
| 5,354,682 | 10/1994 | Kingdon et al. | 435/214 |
| 5,418,130 | 5/1995 | Platz et al. | 435/2 |

FOREIGN PATENT DOCUMENTS

| AT7606505 | 11/1978 | European Pat. Off. . |
|---|---|---|
| AT8003781 | 4/1982 | European Pat. Off. . |
| 0159311A1 | 10/1985 | European Pat. Off. . |
| 0159311B1 | 10/1985 | European Pat. Off. . |
| 0506704B1 | 10/1992 | European Pat. Off. . |
| AT368883 | 11/1982 | Germany . |
| 4325872C | 8/1994 | Germany . |
| WO91/02532 | 3/1991 | WIPO . |

OTHER PUBLICATIONS

Barrowcliffe, *Dev. Biol. Stand*, 81 (1993), "Viral inactivation vs Biological Activity", pp. 125–135, Abstract in MED-LINE, AN 94229366, 1993.
Duffy et al. J. of Biological Chemistry 267(24): 17006/17011 (1992).
Lindhout et al. Biochemistry 21: 5494–5502 (1982).
Batzri et al., Single Bilayer Liposomes Prepared Without Sonication, Biochimica et Biophysica Acta, 298: 1015–1019 (1973).
Szoka et al., Proc. for Prep. of Liposomes With Large Internal Aqueous Space and High Capture by Reverse-Phase Evap., Proc. Natl. Acad. Sci., vol. 75, No. 9, pp. 4194–4198 Sep. (1978).
Barenholz et al., A Simple Method for the Preparation of Homogeneous Phospholipid Vesicles, Biochemistry 16, #12 pp. 2806–2810 (1977).
Teng et al., Production of Factor X and Factor $X_a$ Variants with Thrombin, Acutin and by Autolysis. Thrombosis Research, vol. 22 1981 pp. 213–220.
Giles et al., The Coagulant–Active Phospholipid Content is a Major Determinant of In Vivo Thrombogenicity . . . , Blood, vol. 59, No. 2, pp. 401–407 (1982).
D. Papahadjopoulos, Optimal Liposomal Drug Action: From Serendipity to Targeting, Liposome Technology, 2nd Edition, vol. III, pp. 1–13.
Juliano et al., Interactions of Lipid Membranes With Blood Cells & Proteins: Implications for Drug Delivery & For Biocompatibility, Liposome Technology, 2nd ED., vol. III, pp. 15–25.
Bajaj et al., Simultaneous Purification of Bovine Prothrombin and Factor X, J. of Biol. Chem., vol. 248, No. 22, pp. 7729–7741 (1973) Nov.
Brummelhuis, Methods of Plasma Protein Fractionation, pp. 117–125, Acad. Press (1980).
Zumbuehl et al., Liposomes of Controllable Size in the Range of 40 to 180 NM By Defined Dialysis of Lipid/Detergent Mixed Micelles, Biochimica et Biophysica Acta, 640: 252–262 (1981).
Olson et al., Preparation of Liposomes of Defined Size Distribution By Extrusion Through Polycarbonate Membranes, Biochimica et Biophysica Acta, 557: 9–23 (1979).
Hope et al., Production of Large Unilamellar Vesicles by a Rapid Extusion Procedure, Biochimica et Biophysica Acta, 812: 55–65 (1985).

*Primary Examiner*—Chhaya D. Sayala
*Attorney, Agent, or Firm*—Foley & Lardner

[57] ABSTRACT

The invention relates to a stable preparation which comprises a protein that is bound in and/or on lipid vesicles and that was treated for the inactivation of potentially present viruses. Further, the invention relates to methods for the production of a stable preparation for the treatment of blood coagulation disorders, wherein a protein is bound in and/or on lipid vesicles, and the method comprises a step in which the protein lipid complex is subjected to a treatment for the inactivation of potentially present viruses.

24 Claims, No Drawings

STABLE PREPARATION FOR THE TREATMENT OF BLOOD COAGULATION DISORDERS

The invention relates to a stable preparation which comprises a protein, wherein the preparation is subjected to a method for virus inactivation.

BACKGROUND OF THE INVENTION

As a protein, a coagulation active protein is suitable above all, whereby the preparation is suitable for the treatment of blood coagulation disorders. Also, proteins and/or polypeptides with antigenic determinants are possible. An immunologically effective protein has above all an importance as an immunizing agent. In addition, diverse enzymes and/or enzyme inhibitors are understood as proteins as well as other phamacologically effective proteins.

Coagulation disorders of blood occur when for example the coagulation time deviates from the standard value due to the lack of a coagulation component. The disorders can be inherited as well as acquired through disease conditions.

Hemophilia A is one of the most frequently occurring inherited coagulation disorders. Patients with hemophilia A are prone to frequent hemorrhages as a result of a lack of Factor VIII which can be treated with Factor VIII concentrates. However, in about 15% of the patients the occurrence of Factor VIII neutralizing antibodies, so-called inhibitors, results whereby a therapy with Factor VIII concentrates is hardly possible.

For the treatment of hemophilia A inhibitor patients, complex mixtures of coagulation factors have proven themselves. The activated prothrombin complex FEIBA® (Immuno) has a "factor eight inhibitor bypassing activity".

In lieu of Factor VIII concentrates, it was also attempted to treat hemophilia A with a mixture of coagulation factor Xa and phospholipids. In U.S. Pat. No. 4,610,880, the treatment of hemophilic dogs with a mixture of Factor Xa and phospholipid vesicles is described. This mixture was not stable, for which reason a Factor Xa-containing solution and a suspension of phospholipid vesicles had to be freshly mixed immediately before use. It is stressed that the mixture ratio must be selected in such a way that hemostasis is achieved but thromboses are not caused.

It is known that phospholipid vesicles in combination with Factor Xa increase the danger of thrombosis. On the basis of an in vivo stasis model with rabbits in Blood 59, 401–407 (1982), the increased thrombogenicity of Factor Xa is described when this was tested together with synthetic phospholipids (phosphatidyl choline/phosphatidyl serine lipid vesicles, PCPS vesicles). The danger of thrombosis after administration of prothrombin complex concentrates is also attributed to the combination of coagulation active phospholipids and activated coagulation factors.

It is known from U.S. Pat. No. 4,348,384 to incorporate the coagulation factors Factor VIII and IX in liposomes. Therewith, a preparation which can be orally or intestinally administered for the treatment of hemophilia A or B is made available. Here, the liposomes have a size of 1 μm and protect the Factor VIII or Factor IX from a premature digestion. The administration of these preparations holds no danger of thrombosis because it does not occur intravenously.

The instability of activated coagulation factors in storage is known. A method is known from Thrombosis Research 22, 213–220 (1981) which permits an as stable as possible beta-Factor Xa preparation to be obtained. According to this method, beta-Factor Xa is stored refrigerated in 50% glycerin at pH 7.2 in 0.03M imidazol buffer. However, a further conversion to inactive fragments also occurs in this method even at 4° C. In a similar manner, the instability of Factor Xa in stabilizing glycerol-water mixtures is also described in J. Biol. Chem. 248, 7729–7741 (1973).

SUMMARY OF THE INVENTION

The object of the invention is to make available a stable preparation for the treatment of blood coagulation disorders comprising a coagulation active protein.

A further object of the invention is to make available a stable preparation which comprises a protein and is subjected to a treatment for inactivation of potentially existing viruses.

The above named objects are solved according to the invention through a stable preparation comprising a complex of suitable proteins and lipids in vesicular form. It has been demonstrated that the stability of an activated coagulation factor is increased in an unexpected manner through the association of an activated coagulation factor such as Factor Xa on a phospholipid in vesicular form, i.e. through the binding in and on a lipid vesicle. The present invention possesses exceptionally good storage stability in solution, frozen form and lyophilized form. It can even be demonstrated that an activated coagulation factor is protected from physical inactivation such as for example in a lyophilization process or in a treatment for the purpose of virus inactivation. The in vivo activity of the activated coagulation factor is also maintained, which is also a measure for the stability of the preparation.

Due to the unexpected high stability of the preparations according to the invention, it is possible to subject a protein, for example a blood factor of intrinsic and/or extrinsic coagulation pathways respectively and/or a cofactor and/or an inhibitor of blood coagulation and/or a coagulation active lipoprotein, such as for example Lp(a), or an antigen, especially a viral antigen, in the form bound in or on lipid vesicles to a treatment for virus inactivation, preferably a chemical and/or physical treatment and especially a heat treatment. Thereby, the biological activity and/or antigenicity remains largely maintained.

DETAILED DESCRIPTION OF THE INVENTION

A preparation according to the invention is considered as stable when the activity of the protein is retained to more than 40%, preferably more than 50% through measures such as lyophilization and reconstitution in the absence of customary stabilizers in unbuffered solutions and/or when more than 40% of the activity of the active protein, preferably more than 50%, most preferably more than 60%, is retained by the storage of an aqueous solution of the preparation in the absence of customary stabilizers at 22° C. after 20 hours.

The term "coagulation active protein" comprises, according to the invention, an activated or non-activated blood factor of intrinsic and/or extrinsic coagulation, a cofactor of blood coagulation and a coagulation active lipoprotein, such as for example Lp(a), as well as combinations thereof.

The advantage of an antigen in a preparation according to the invention is above all that, simultaneously with an increased stability of the preparation, the lipid components have an adjuvant effect. Thereby, the preparation according to the invention is especially suitable as an immunizing agent. The antigen is for example a recombinant protein and/or polypeptide recombinantly produced. Thereby, depending on the type of the cell culture, a contamination with infectious agents can occur. Through the preparation according to the invention, which is considered as safe in view of a transmission of infectious agents, an infection is however effectively avoided.

As determined by the exceptionally high stability, which was also established in vivo after infusion of the preparation of the invention, the preparation is exceptionally suitable for the treatment of patients, especially for the treatment of blood coagulation disorders.

Based on its structure, which is characterized by a protein and a lipid component, a complex of a thrombocytic coagulation active substance, i.e. for example a blood coagulation factor that is naturally present in thrombocytes, is suitable according to the invention as a thrombocyte substitute alone or in combination with further coagulation active substances and a lipid vesicle, and, for the treatment of blood coagulation disorders which are connected with a lack of activated thrombocytes. For one thing, the complex according to the invention imitates the form of a blood platelet, for another, functional similarities can be established, such as for example aggregation capability in a protein solution or in the presence of calcium ions or the adsorption on structural proteins of the collagen type. Therefore, the preparation according to the invention can fulfill functions of thrombocytes.

An in vitro test for the determination of the coagulation time of hemophilia A inhibitor plasma serves for the assessment of the effectiveness of the preparation according to the invention for the treatment of hemophilia A inhibitor patients. An effective preparation shortens the coagulation time by at least 50% and preferably to the coagulation time of normal plasma.

It has been surprisingly demonstrated that, through the association of coagulation factor Xa and phospholipid vesicles, the production of a preparation with good storage stability and a high half-life in a Factor VIII inhibitor plasma is possible. The preparation according to the invention is preferably stored in lyophilized form. The lyophilized preparation can be reconstituted to a solution which comprises the complex in vesicular structure. An addition of carbohydrates such as mono- or disaccharide, approximately in an amount of 3–20% (w/w) is advantageous. The stability of the complex according to the invention is further increased in the presence of small amounts of calcium ions. It has been further demonstrated that the complex of coagulation factors and lipid vesicles is not thrombogenic in the pharmaceutical preparations for the treatment of coagulation disorders.

As an active component, the preparation according to the invention comprises a vitamin K dependent protein, for example a factor selected from the group of Factors IIa, VIIa, IXa and Xa, preferably Xaβ. Furthermore, additional proteins can be included, such as for example the Factors II, VII, IX, X, protein C, activated protein C, protein S and protein Z. It has emerged that the combination of Factor Xa with at least one of the named proteins is particularly effective. An additional amount of Factor VIII, activated Factor VIII, vWF, Factor V and/or activated Factor V is advantageous. A further embodiment of the preparation according to the invention comprises a complex of an activated blood coagulation factor and lipid vesicles and additionally "tissue factor" or fragments of "tissue factor".

The proteins included in the complex are preferably human and isolated from a plasma fraction or of recombinant origin. Based on a potential infectiousness, a treatment for the inactivation of infectious agents, such as for example viruses or prions, is appropriate. It is recommended to undertake a heat treatment of the substances or the complex of the proteins and lipid vesicles. The treatment can ensue for example according to EP 0 159 311.

According to a preferred embodiment, a complex of a highly purified Factor Xa (at least 100 U/mg protein), which is free of infectious agents by a treatment for virus inactivation, with phospholipid vesicles is made available.

Based on its stability, the preparation is to be made available as a liquid preparation without anything further, i.e. without addition of the commonly used stabilizers such as carbohydrates (saccharose) or protease inhibitors (aprotinin).

However, the preparation can in addition also be stored in liquid deep-frozen form or in lyophilized form wherein a polysaccharide amount is advantageous in water removal.

According to the invention, phospholipids in vesicular form can be used as lipid vesicles. The phospholipids can be synthetic or of natural origin. Thereby, a standardized mixture of chemically pure phospholipids is advantageous.

The lipid vesicles can be prepared in various ways such as by sonification of phospholipid dispersions (Barenholz et al., Biochemistry 16, 2806–2810, 1977), the reversed phase evaporation technique (F. Szoka and D. Paphadjopoulos, Proc. Natl. Acad. Sci. USA 75, 4194–4198, 1978), the ethanol injection method (S. Batzri and E. D. Korn, Biochem. Biophys. Acta 298, 1015–1019, 1973) or also the removal of detergents from mixed micelles by dialysis methods (O. Zumbuehl and H. G. Weder, Biochem. Biophys. Acta 640, 252–262, 1981). Furthermore, the extrusion method according to Olson et al. (Biochem. Biophys. Acta 557, 9–23, 1979) can also be used. A dispersion of multilamellar vesicles is prepared by hydration of a lipid film which can be obtained preferably by evaporation of solutions of the lipids in organic solvents with the aid of a rotary evaporator. This dispersion is subsequently pressed through two stacked polycarbonate filters with nitrogen pressure.

This method should be carried out at a temperature at which the phospholipids are found in a liquid-crystalline state (at least 5° C., preferably at least 10° C. above the phase transition temperature, $T_M$). Optionally, a repeated freeze-thaw cycle is introduced before the extrusion (M. J. Hope et al., Biochem. Biophys. Acta 812, 55–65, 1985). Furthermore, an embodiment has proven to be particularly advantageous. Here, the dispersion of multilamellar vesicles is produced as outlined above, lyophilized, and reconstituted again with water. Thereby, the subsequent extrusion can be carried out particularly easily and also with very high lipid concentrations for example, 100 mg lipid/ml).

For the production of the complex according to the invention, the described lyophilization step can be carried out after mixing the vesicle dispersion with the protein, here preferably coagulation factor Xa. After reconstitution, the complex according to the invention can be further extruded. A further possibility for the production of the complex according to the invention is the mixing of the components in the presence of a tenside and the subsequent removal of the tenside, for example by dialysis. A direct hydration of the lipid film with a solution of proteins is also particularly advantageous, wherein optionally lyophilization and reconstitution can be done, whereby the extrusion is made easier. Optionally, in the last variation, the additional lyophilization step can be dispensed with. A direct mixing of the prepared vesicles with the protein preferably in the presence of charged particles or under conditions which permit the incorporation of the protein in and on the lipid vesicles (concentration, selection of proteins with hydrophobic properties, etc.) is also conceivable.

For the extrusion process, particularly filters with a diameter of about 30 to 1000 nm can be used. The typical size of the lipid vesicles (determined by the method of dynamic light scattering) is in the order of 30 to 900 nm, preferably 100 to 500 nm.

The stability of the produced complex is improved when charged particles, for example calcium ions, preferably 1–10 mM, are present. Based on the binding of the coagulation proteins in and on the lipid vesicles, a purification and isolation of the complex per se is possible. This can occur by gel filtration or ultracentrifugation.

The glycerophospholipids phosphatidyl serine, phosphatidic acid, phosphatidyl glycerol, diphosphatidyl glycerol (cardiolipin) and also phosphatidyl ethanolamine which can exhibit a negative charge are among the suitable phospholipids and are used preferably alone or also combined in a mixture with neutral phospholipids such as phosphatidyl choline and sphingomyelin, wherein the binding by addition of calcium ions is favored. As anionic components, the use of other lipids, such as for example sulfatides or also dicetylphosphate, phosphatidyl methanol, phosphatidyl-$\beta$-lactate and oleic acid is also possible. However, the exclusive use of neutral phospholipids such as phosphatidyl choline or sphingomyelin is also conceivable. However, substances obtained through chemical modification such as the lipid derivatives of the polyethylene glycols or substances from the classes of lysophospholipids or glycolipids are also usable. The use of lipids which can exhibit a positive charge, such as for example stearylamine, dimethyldioctadecyl ammonium bromide (DDAB), or also cationic lipids of the type of the 1,2-diacyl-3-trimethyl ammonium propanes (TAP) or the 1,2-diacyl-3-dimethyl ammonium propanes (DAP) is also conceivable.

A preferred embodiment comprises the use of lipids with anti-viral effect, for example alkylphospholipids (see EP 0 506 704 B1).

For stabilization, the phospholipid vesicles can comprise up to 80 Mol % cholesterol as an additional component. It is to be emphasized that all specified lipids can also be used as a sole component, optionally also under addition of cholesterol.

For the formation of the complex the lipid vesicles can be found in the gel state or in the liquid-crystalline state, however, the use of systems in the liquid-crystalline state is more favorable. In a version of the invention, lipid vesicles comprised of 1,2,-dioleoyl-sn-glycero-3-phosphochotine and 1-palmitoyl-2-oleoyl-sn-glycero-3-phosphoserine are used (for example in a ratio of PC/PS=80/20 (w/w), see Example 1) which are liquid-crystalline at room temperature. The use of phospholipids with unsaturated side chains can, however, lead to a reduced stability by virtue of oxidation. Therefore, for the chemical stability of the vesicles, the use of lipids with fatty acid groups such as those of myristic acid, palmitic acid (Examples 2 and 3 or stearic acid, which are however normally found in the gel state, is preferable. The use of these lipids has been proven as particularly advantageous, however, in mixtures with cholesterol.

The invention is more closely illustrated through the following Examples.

Production of phospholipid vesicles

EXAMPLE 1

Production of Multilamellar Vesicles

In a 100 ml flask, 40.0 mg 1,2-dioleoyl-sn-glycero-3-phosphocholine and 10.0 mg 1-palmitoyl-2-oleoyl-sn-glycero-3-phosphoserine (Avanti Polar Lipids) are dissolved in 5 ml chloroform and evaporated with the aid of a rotary evaporator under reduced pressure and a temperature of 30° C. After complete removal of the solvent, a vacuum was still held over 30 min at 30 mbar and subsequently dried over a time period of six hours in high-vacuum at 0.1 mbar. The phospholipid film was subsequently hydrated by addition of 5 ml of buffer (20 mM Tris, 150 mM NaCl, pH 7.4) and gentle shaking over one hour at room temperature.

EXAMPLE 2

After formation of a dispersion of multilamellar vesicles according to Example 1, the vesicles were extruded 10 times with $N_2$ pressure through two stacked 100 mm polycarbonate filters laid on top of each other (10 ml thermobarrel extruder, Lipex Biomembranes Inc., Vancouver, Canada). The determination of the particle size of the vesicles produced in this way with the aid of dynamic light scattering (Malvern Zetasizer 4) resulted in a average diameter of about 100 nm.

EXAMPLE 3

From 35.0 mg 1,2-dimyristoyl-sn-glycero-3-phosphocholine (Nattermann Phospholipid GmbH) and 15.0 mg 1,2-dimyristoyl-sn-glycero-3-phosphoserine (Avanti Polar Lipids) in 5 ml chloroform/methanol mixture (2:1, v/v), a phospholipid film was produced as described in Example 1. After addition of 5 ml of buffer (20 mM Tris, 150 mM NaCl, pH 7.4), the film was hydrated at 50° C. by using a rotary evaporator and extruded at 50° C. as described under Example 2.

EXAMPLE 4

From a mixture of 35.0 mg 1,2-dipalmitoyl-sn-glycero-3-phosphocholine (Nattermann Phospholipid GmbH) and 15.0 mg 1,2-dimyristoyl-sn-glycero-3-phosphoserine (Avanti Polar Lipids), phospholipid vesicles were produced as described in Example 3. The hydration of the film and the extrusion also occurred at 50° C.

EXAMPLE 5

From a mixture of 40.0 mg 1,2-dioleoyl-sn-glycero-3-phosphocholine (Sigma) and 10.0 mg 1,2-dioleoyl-sn-glycero-3-phosphoglycerol or 17.5 mg cardiolipin from bovine heart (Sigma), phospholipid vesicles were produced as described under Example 1 and 2.

EXAMPLE 6

From a mixture of 40.0 mg 1,2-dioteoyl-sn-glycero-3-phosphocholine and 10.0 mg 1,2-dioleoyl-sn-glycero-3-phosphate (Sigma), phospholipid vesicles were produced as described under Example 1 and 2.

EXAMPLE 7

From a mixture of 35.0 mg 1,2-dioleoyl-sn-glycero-3-phosphocholine, 10.0 mg 1-palmitoyl-2-oleoyl-sn-glycero-3-phosphoserine (Avanti Polar Lipids) and 5 mg phosphatidyl inositol form Soya beans (Sigma), phospholipid vesicles were produced as described under Example 1 and 2.

EXAMPLE 8

5 to 80 Mol % cholesterol (Sigma) was added to the mixtures of phosphatidyl choline, phosphatidyl serine, phosphatidyl glycerol, phosphatidic acid and/or phosphatidyl inositol described in Examples 1 to 7 and extruded as described under the respective Examples.

EXAMPLE 9

After hydration of the phospholipid film, the dispersions from Examples 1–8 were shock frozen (liquid $N_2$) and thawed at 37° C. (Examples 2, 5–8) and/or 50° C. (Examples 3 and 4). This process was repeated four times. The multilamellar vesicles produced in this way were extruded as described in the respective Examples. The vesicle preparations resulting therefrom had an average diameter of 100 nm.

EXAMPLE 10

As described in the Examples 1–9, multilamellar vesicles were produced through hydration of phospholipid films. The dispersions obtained in this way were frozen at −80° C. and lyophilized. After reconstitution of the lyophilizates with the corresponding volumes of $H_2O$, extrusion was done as described under the respective Examples.

EXAMPLE 11

The production of phospholipid vesicles according to Examples 1–10 was carried out in 150 mM NaCl instead of Tris buffer. The size determination of the vesicles with the aid of dynamic light scattering resulted in a nearly identical size distribution in comparison to vesicles that were produced with buffered solution.

EXAMPLE 12

1,2-dioleoyl-sn-glycuero-3-phosphocholine

A mixture of 8.0 mg 1,2-dioleoyl-sn-glycero-3-phosphocholine (Avanti Polar Lipids), 2.0 mg phosphatidyl inositol from Soya beans (Sigma) and 10.0 mg sodium choiate (Sigma) was added in a 50 ml round flask and dissolved in 10 ml of a chloroform/methanol mixture (1:1, v/v). Then, this was evaporated in a rotary evaporator at a bath temperature of 20° C. under reduced pressure until dry, taken up in 10 ml absolute methanol and evaporated again. The film produced in this way was taken up under shaking with 2 ml buffer (20 mM Tris, 150 mM NaCl, pH 7.4). For the production of the vesicles, the clear solution was subsequently dialyzed 24 h against the same buffer at 4° C. The determination of the particle size with the aid of dynamic light scattering resulted in an average diameter of about 70 nm.

Lyophilization of phospholipid vesicles in the presence of saccharose

EXAMPLE 13

Saccharose to a concentration of 3–20% (w/v) was added to the vesicles produced corresponding to the Examples 1–12. Subsequently, this was frozen at −80° C. and lyophilized. After reconstitution of the lyophilizate, the determination of the size with the aid of dynamic light scattering resulted in an average diameter of about 100 nm. The electron microscopic examination of this solution resulted in a size distribution of about 80 to 130 nm according to visualization with the negative staining method.

Production of a complex of Factor Xa and phospholipid vesicles

EXAMPLE 14

Colyophilization

Factor Xa was produced as follows:

A solution of the prothrombin complex preparation (corresponding to 50,000 U Factor X/l) produced according to the methods of Brummelhuis (Methods of Plasma Protein Fractionation, J. M. Curling (editor), pp 117, Acad. Press., 1980) and heat treated according to the method of EP 0 159 311, was treated in the presence of 12 % (v/v) Tween® 80 one hour at pH 7.0 and room temperature. Subsequently, this was diluted, mixed With trisodium citrate dihydrate (7.0 g/l), and the proteins of the prothrombin complex precipitated at pH 7.0 by addition of 400 ml 1M barium chloride solution. The precipitate was washed and resuspended in a 25% (w/v) ammonium sulfate solution containing 50 mM benzamidine HCl. The non-dissolved matter was separated and the solution was brought to 80% saturation with ammonium sulfate in order to precipitate the proteins again. The precipitate was dissolved in buffer and rebuffered chromatogaphically over Sephadex®-G25 against 25 mM trisodium citrate buffer containing 100 mM NaCl and 1 mM benzamidine HCl, pH 6.0.

The protein containing fractions were further purified by means of a DEAE Sepharose® fast flow column. By increasing the sodium chloride concentration in the citrate buffer (25 mM, pH 6.0), Factor X was eluted separated from the other prothrombin complex proteins. The obtained fraction was rebuffered against 20 mM Tris HCl buffer containing 150 mM sodium chloride and 2 mM calcium chloride (pH 7.4). Subsequently, this was mixed with 0.14 mg RVV (Russel's viper venom, a protease from Vipera russellii, Pentapharm) per 100 U FX and stirred one hour at room temperature. The generated Factor Xa was then purified chromatographically with a benzamidine Sepharose® column and concentrated through ammonium sulfate precipitation and subsequently chromatographed over Sephadex®-G25 for the removal of the salt. The produced Factor Xa preparation had a specific activity of at least 100 U Factor Xa/mg protein.

For the production of the complex, a vesicle preparation produced according to the Examples 1–12 was mixed, with or without 2.5 mM calcium chloride, to the Factor Xa fraction. The solution was lyophilized.

After reconstitution, the effectiveness of the preparation in the FEIBA test (test description see AT 350 726) was tested. As a comparison for this, the FEIB activity of the non-complexed Factor Xa was determined. Before the lyophilization, the FEIB activity amounted to 1700 U/ml in both cases. After the lyophilization and reconstitution, 1650 U/ml was recovered in the case of the Factor Xa/PCPS complex. The loss of FEIB activity was much larger in the case of non-complexed Factor Xa. Only 1220 U/ml was recovered.

EXAMPLE 15

Extrusion of a Colyophilizate

A colyophilizate produced according to Example 14 comprising 1000 U Factor Xa as well as 50.0 mg of a phospholipid preparation produced according to Example 6 of 40.0 mg 1,2-dioleoyl-sn-glycero-3-phosphocholine and 10.0 mg 1,2-dioleoyl-sn-glycero-3-phosphate was taken up with water in the original volume and extruded twice at a temperature of 20° C. through two stacked 400 nm polycarbonate filters (Lipex Biomembranes, Inc.). The determination of the particle size with the aid of dynamic light scattering (Malvern Zetasizer 4) resulted in an average diameter of about 450 nm.

EXAMPLE 16

Coextrusion

As described under Example 1, a film was produced from a phospholipid mixture. This was hydrated with a Factor Xa containing solution from Example 14 with or without 2.5 mM calcium chloride. After hydration of the film, it was proceeded as in the Examples 2, 9 and 10 and extruded. Thereby, Factor Xa was complexed with phospholipid vesicles. Saccharose in a concentration of 3–20% (w/v) could be added to the complex produced in this way in order to subsequently lyophilize.

Production of a complex of activated protein C, Factor Xa and phospholipid vesicles

EXAMPLE 17

A film was prepared as described under Example 1 from a phospholipid mixture. This was hydrated with the Factor Xa containing fraction from Example 14 as well as with activated protein C in a 20 mM Tris HCl buffer containing 150 mM NaCl and 5 mM $CaCl_2$, pH 7.4. The mixture containing 10 U FXa/ml, 10 U APC/ml and 10 mg phospholipid/ml was lyophilized.

Purification of the complex of Factor Xa and PCPS vesicles

EXAMPLE 18

A preparation containing Factor Xa and PCPS vesicles was produced according to the method described in the Examples 14 or 16, wherein saccharose in a final concentration of 5% (w/v) was added to the Factor Xa phospholipid preparation. The lyophilizate was dissolved in water in such a way that the prepared solution contained 2.4 U Factor Xa/ml and 1 mg/ml PCPS vesicles. A column packed with SUPEROSE 6 HR 10/30 (highly cross-linked agarose), Pharmacia, was equilibrated with a buffer (20 mM Tris HCl containing 150 mM NaCl, 0.1% albumin, 0.01% TWEEN 20 (polyoxyethylene sorbitan monolaurate), 1 mM $CaCl_2$, pH 7.4). 500 µl of the PCPS vesicles and Factor Xa containing preparation were chromatographed over the column with a flow rate of 0.4 ml/minute.

In the eluate stream, the UV absorption at 254 nm was measured. The fraction of the exclusion volume containing a complex of PCPS vesicles and Factor Xa was collected.

EXAMPLE 19

A lyophilizate produced according to Example 14 was reconstituted with water such that the finished solution contained 5 U Factor Xa and 5 mg PCPS per ml. 0.5 ml of this solution were mixed with 1 ml of a 30% (w/v) ficoll 400 solution (Pharmacia, in 150 mM sodium chloride solution). This mixture was placed in an ultracentrifugation tube and overlaid with 3 ml of 10% ficoll solution. Finally, this was overlaid with 150 ml NaCl solution and subsequently centrifuged by use of a swing out rotor for 30 minutes at 100,000 g and room temperature.

The layer containing the purified Factor Xa/PCPS complex with lower density than the aqueous solution could be separated as a supernatant.

EXAMPLE 20

A complex comprising activated protein C, Factor Xa and phospholipid vesicles was produced according to Example 17. The lyophilized complex was reconstituted with water and concentrated to a third of the starting volume by centrifugation over ultrafree-MC filter units, exclusion limit 100,000 Daltons (polysulphone membranes, Millipore), 30 minutes at 4000 rpm. The retained material obtained in this way contained the purified complex of activated protein C, Factor Xa and phospholipid vesicles.

Stability of the complex of protein and phospholipids

EXAMPLE 21

Stability of a Factor Xa/PCPS Vesicle Complex in the Lyophilization Process

PCPS vesicles were produced as described in Examples 1 and 2. These were subsequently mixed with Factor Xa, which was produced as described in Example 14, such that the preparation comprised 0.5 mg phospholipid vesicles per ml and 47 U Factor Xa in an aqueous solution of 150 mM/l NaCl and 5 mM/l $CaCl_2$. The complex was lyophilized. As a comparison for this, Factor Xa was lyophilized in the same concentration, however without PCPS vesicles. Subsequently, according to German patent application P4325872.7, the Factor Xa activity was determined in the lyophilized preparations after reconstitution with distilled water in the starting volumes and compared with the Factor Xa amount before the lyophilization (see Table).

|  | Factor Xa activity (%) | |
| --- | --- | --- |
|  | before lyo | after lyo |
| PCPS/FXa-complex | 100 | 51 |
| Factor Xa | 100 | 20 |

The Table shows the stabilizing influence of vesicular phospholipid on Factor Xa in the copreparation.

EXAMPLE 22

Stability of a Factor Xa/PCPS Vesicle Complex in Solution

A complex of PCPS vesicles and Factor Xa was produced as described in Example 21 and lyophilized. After the reconstitution, the solution was stored at 22° C. over 20 hours. Subsequently, the activity of Factor Xa was determined. The following Table shows the stability of Factor Xa in the PCPS vesicle complex in comparison to non-complexed Factor Xa.

|  | Factor Xa activity (%) | |
| --- | --- | --- |
|  | 0 h | 20 h |
| PCPS/FXa-complex | 100 | 67 |
| Factor Xa | 100 | 34 |

EXAMPLE 23

Stability of a Protein C/Factor Xa/PCPS Vesicle Complex in the Lyophilization

A complex comprising protein C, Factor Xa and PCPS vesicles was produced analogously to Example 17 and lyophilized. The preparation contained 0.5 mg phospholipid vesicles/ml, 10 U protein C/ml and 47 U Factor Xa/ml in an aqueous solution of 150 mM NaCl. As a comparison for this, protein C and Factor Xa was lyophilized at the same concentrations, however without PCPS vesicles. Subsequently, the Factor Xa activity was determined as in Example 21 and the protein C activity was determined by use of a chromogenic test (Immunochrom PC, Immuno) in the lyophilized preparations after reconstitution with distilled water in the starting volumes and compared with the respective amount of Factor Xa and protein C before the lyophilization (see Table).

|  | protein C activity (%) | | Factor Xa activity (%) | |
| --- | --- | --- | --- | --- |
|  | before lyo | after lyo | before lyo | after lyo |
| PCPS/protein C/ FXa complex | 100 | 89 | 100 | 84 |
| protein C | 100 | 41 | — | — |
| Factor Xa | — | — | 100 | 23 |

The Table shows the stabilizing influence of phospholipid vesicles on protein C and Factor Xa in the complex.

EXAMPLE 24

Stability of a Protein C/FXa/PCPS Vesicle Complex in Solution

A complex of protein C, Factor Xa and PCPS vesicles and Factor Xa was produced as described in Example 23 and lyophilized. After the reconstitution, the solution was stored at 22° C. over 20 hours. Subsequently, the activity of protein C and Factor Xa was determined. The following Table shows the increased stability of protein C and Factor Xa in the PCPS vesicle complex in comparison to the non-complexed factors.

|  | protein C activity (%) | | Factor Xa activity (%) | |
| --- | --- | --- | --- | --- |
|  | 0 h | 20 h | 0 h | 20 h |
| PCPS/protein C/ FXa-complex | 100 | 100 | 100 | 88 |
| protein C | 100 | 65 | — | — |
| Factor Xa | — | — | 100 | 9 |

In vitro characterization of the protein/phospholipid complexes.

EXAMPLE 25

For the testing of the effectiveness of the preparation according to the invention, the following test system was used.

100 µl of FVIII inhibitor plasma (45 Bethesda Units/ml) were mixed in a coagulometer tube with 100 µl 20 mM Tris HCl buffer containing 150 mM NaCl, pH 7.4 (TBS) and recalcified with a further 100 µl of a 0.025M calcium chloride solution. Immediately after addition of the sample to be analyzed (100 µl), the coagulation time of the mixture was determined by use of a coagulometer (Schnitger/Gross) at 37° C.

When pure TBS buffer was employed as a sample in the represented test substance, the coagulation time amounted to 820 seconds. In comparison to this, the coagulation time of normal plasma in this test system was about 350 seconds.

A preparation produced according to Example 16 was tested at a concentration of 0.88 mU Factor Xa and 0.3 µg phospholipid/ml. As an additive, either 0.1 U FEIBA produced according to the method of AT 368 883 or 0.1 U recombinant Factor VIIa (Novo Nordisk) were tested. Also, a mixture of the FEIBA preparation (0.01; 0.1; 1.0 U/ml) or of Factor X (0.01; 0.1; 1.0 U/ml) produced according to the method from Example 14 with 0.3 µg/ml phospholipid vesicles produced according to the method from Example 1 and 2 were tested. The influence of the tested substances on the coagulation time is given in the following Table.

Shortening of the coagulation time by a preparation containing the complex of coagulation protein and phospholipid vesicles.

| test substance | concentration (mU/ml) | | | | coagulation time (s) |
| --- | --- | --- | --- | --- | --- |
|  | FXa | FEIBA | FVIIa | FX |  |
| Factor Xa/PCPS | 0.88 | — | — | — | 125 |
| Factor Xa/FEIBA/PCPS | 0.88 | 100 | — | — | 82 |
| Factor Xa/Factor VIIa/PCPS | 0.88 | — | 100 | — | 131 |
| FEIBA/PCPS | — | 10 | — | — | 409 |
|  |  | 100 |  |  | 167 |
|  |  | 1000 |  |  | 120 |
| Factor X/PCPS | — | — | — | 10 | 814 |
|  |  |  |  | 100 | 425 |
|  |  |  |  | 1000 | 336 |

Biological in vitro activity of various phospholipid vesicle types

EXAMPLE 26

Phospholipid vesicles comprising mixtures of various phospholipid types in different composition were produced as described in the Examples and processed to copreparations with Factor Xa. The FXa phospholipid vesicle complex resulting therefrom was examined as described in Example 25 on the coagulation shortening effect of FVIII inhibitor plasma. The results (coagulation times) are in the following Table:

| vesicle type | composition w/w % | conc./ml in test substance | | coagulation time (s) |
| --- | --- | --- | --- | --- |
|  |  | mU FXa | µg lipid |  |
| DOPC | 80 | 1.375 | 6.25 | 62 |
| POPS | 20 |  |  |  |
| DOPC | 70 | 1.375 | 6.25 | 65 |
| POPS | 20 |  |  |  |
| CHOL | 10 |  |  |  |
| DOPC | 60 | 1.375 | 6.25 | 57 |
| POPS | 20 |  |  |  |
| CHOL | 20 |  |  |  |
| DOPC | 50 | 1.375 | 6.25 | 56 |
| POPS | 20 |  |  |  |
| CHOL | 30 |  |  |  |
| DOPC | 40 | 1.375 | 6.25 | 69 |
| POPS | 20 |  |  |  |
| CHOL | 40 |  |  |  |
| DOPC | 30 | 1.375 | 6.25 | 58 |
| POPS | 20 |  |  |  |
| CHOL | 50 |  |  |  |
| POPS | 95 | 1.375 | 6.25 | 73 |
| PI | 5 |  |  |  |
| POPS | 90 | 1.375 | 6.25 | 77 |
| PI | 10 |  |  |  |
| POPS | 80 | 1.375 | 6.25 | 71 |
| PI | 20 |  |  |  |
| DOPC | 80 | 1.375 | 6.25 | 135 |
| PI | 20 |  |  |  |
| DOPC | 80 | 1.375 | 6.25 | 66 |
| POPS | 15 |  |  |  |
| PI | 5 |  |  |  |
| DOPC | 80 | 1.375 | 6.25 | 89 |
| POPS | 10 |  |  |  |
| PI | 10 |  |  |  |
| DOPC | 80 | 1.375 | 6.25 | 110 |
| POPS | 5 |  |  |  |
| PI | 15 |  |  |  |
| DOPC | 75 | 1.375 | 6.25 | 75 |
| POPS | 20 |  |  |  |

-continued

| vesicle type | composition w/w % | conc./ml in test substance mU FXa | µg lipid | coagulation time (s) |
|---|---|---|---|---|
| PI | 5 | | | |
| DOPC | 70 | 1.375 | 6.25 | 80 |
| POPS | 20 | | | |
| PI | 10 | | | |
| DOPC | 60 | 1.375 | 6.25 | 72 |
| POPS | 20 | | | |
| PI | 20 | | | |
| DOPC | 60 | 1.375 | 6.25 | 85 |
| POPS | 10 | | | |
| PI | 10 | | | |
| CHOL | 20 | | | |
| DOPC | 50 | 1.375 | 6.25 | 82 |
| POPS | 20 | | | |
| PI | 10 | | | |
| CHOL | 10 | | | |
| CLP | 100 | 1.16 | 5.63 | 76 |
| DOPC | 70 | 1.16 | 6.88 | 69 |
| CLP | 30 | | | |
| DMPC | 70 | 1.16 | 8.45 | 91 |
| DMPS | 30 | | | |
| DPPC | 70 | 1.16 | 8.45 | 123 |
| DMPS | 30 | | | |
| DMPC | 50 | 1.16 | 8.45 | 86 |
| DMPS | 30 | | | |
| CHOL | 20 | | | |
| DMPC | 30 | 1.16 | 8.45 | 67 |
| DMPS | 30 | | | |
| CHOL | 40 | | | |
| DPPC | 50 | 1.16 | 8.45 | 100 |
| DMPS | 30 | | | |
| CHOL | 20 | | | |
| DPPC | 30 | 1.16 | 8.45 | 154 |
| DMPS | 30 | | | |
| CHOL | 40 | | | |
| DOPG | 80 | 1.25 | 10 | 77 |
| DOPC | 20 | | | |
| DOPA | 80 | 1.25 | 10 | 67 |
| DOPC | 20 | | | |
| buffer background | | 0 | 0 | 820 |

Legend:
DOPC = 1,2-dioleoyl-sn-glycero-3-phosphocholine
POPS = 1-palmitoyl-2-oleoyl-sn-glycero-3-phosphoserine
CHOL = cholesterol
CLP = diphoshatidyl glycerin (cardiolipin)
PI = phosphatidyl inositol
DMPC = 1,2-dimyristoyl-sn-glycero-3-phosphocholine
DMPS = 1,2-dimyristoyl-sn-glycero-3-phosphoserine
DPPC = 1,2-dipalmitoyl-sn-glycero-3-phosphocholine
DOPG = 1,2-dioleoyl-sn-glycero-3-phosphoglycerin
DOPA = 1,2-dioleoyl-sn-glycero-3-phosphoric acid

EXAMPLE 27

The effectiveness of a complex produced according to Example 14 with 20 mU Factor Xa and 4.96 µg PCPS/ml, and various dilutions thereof, in Factor VIII inhibitor plasma was determined in the following coagulation test immediately after mixing and after an hour incubation at 37° C.:

200 µl of sample were mixed in a coagulometer tube with 100 µl 20 mM Tris HCl buffer containing 150 mM NaCl, pH 7.4 (TBS) and recalcified with a further 100 µl of a 0.025M calcium chloride solution. Immediately after addition of this solution, the coagulation time of the mixture was measured by use of a coagulometer (Schnitger/Gross) at 37° C.

When a 1+1 mixture of FVIII inhibitor plasma (45 Bethesda Units/ml) and TBS buffer was employed as a sample in the represented test substance, the coagulation time amounted to more than 500 seconds.

As a comparison, pure Factor Xa produced according to the method from Example 14 was tested. The results are summarized in the following Table.

Coagulation time of Factor Xa/PCPS and Factor Xa before and after incubation with Factor VIII inhibitor plasma

| dilution of the stock solution | coagulation time (s) | | | |
|---|---|---|---|---|
| | Factor Xa | | Factor Xa/PCPS | |
| | 0 h | 1 h | 0 h | 1 h |
| undiluted | 77 | 161 | 35 | 69 |
| 1:2 | 95 | 236 | 48 | 111 |
| 1:4 | 117 | 349 | 65 | 185 |
| 1:8 | 152 | >500 | 88 | 314 |
| 1:16 | 224 | >500 | 145 | 400 |
| 1:32 | 314 | >500 | 200 | >500 |
| 1:64 | 441 | >500 | 296 | >500 |
| 1:128 | >500 | >500 | 402 | >500 |

The complex of Factor Xa/PCPS according to the invention has a higher stability than non-complexed Factor Xa. In low concentrations, Factor Xa/PCPS also leads to a shortening of the coagulation time after one hour incubation in Factor VIII inhibitor plasma, whereas non-complexed Factor Xa had already lost its coagulation time shortening activity.

In vivo characterization of the protein/phospholipid complexes

EXAMPLE 28

Test on Thrombogenicity

A FEIBA preparation produced according to the method of AT 368 883 was tested for thrombogenicity as a complex with PCPS vesicles and in non-complexed form in the Wessler-Stasis model. The PCPS vesicles were produced according to the method from Example 1 and 2, wherein vesicles of average sizes of 100 nm and/or 50 nm were obtained through a suitable filter choice. 4 U FEIBA and 60 µg PCPS were used per kg rabbit. The thrombogenicity of the FEIBA preparation was not increased by the complex formation with PCPS vesicles. In all cases, no thrombi formation was registered in the stasis model (score=0–1).

Heat treatment of the protein/phospholipid vesicle complexes

EXAMPLE 29

Heat Treatment of a Complex of Factor Xa and PCPS Vesicles

A lyophilizate of Factor Xa and PCPS produced according to Example 14 or 16 was treated according to the method of EP 159 311 for 10 hours at 60° C. and 1 hour at 80° C. The Factor Xa activity of the reconstituted solution amounted to more than 90% of the activity before the heat treatment. With the aid of the method of dynamic light scattering (Malvern Zetasizer 4) the preservation of the vesicular structure could be detected.

EXAMPLE 30

Heat Treatment of a Complex of FEIBA and PCPS Vesicles

A complex of phospholipid vesicles and FEIBA was produced analogously to Example 14 and lyophilized. After reconstitution, the lyophilizate contained 30 U FEIBA/ml and 3.4 mg PCPS/ml in a buffer of 4 g $Na_3citrate \cdot 2H_2O/l$ and 8 g NaCl/l, pH 7.0. A lyophilizate corresponding to this composition was treated according to the method of EP 159

311 for 10 hours at 60° C. and 1 hour at 80° C. The FEIBA activity in the reconstituted solution after heat treatment amounted to more than 90% of the activity before the heat treatment With the aid of the method of dynamic light scattering (Malvern Zetasizer 4) the preservation of the vesicular structure could be detected.

We claim:

1. A storage-stable, virus-safe preparation comprising a coagulation protein that is bound to at least one phospholipid vesicle by a process selected from the group consisting of
   (a) hydration of a phospholipid film with a solution containing the coagulation protein;
   (b) at least one of co-lyophilization, co-extrusion or sonication of a solution containing the phospholipid vesicle and the coagulation protein;
   (c) contacting the phospholipid vesicle and the coagulation protein with a tenside and then dialyzing to remove the tenside; and
   (d) mixing the coagulation protein and the phospholipid vesicle in the presence of charged particles;
   wherein any one of (a)–(d) can bind the coagulation protein to the phospholipid vesicle, and wherein the preparation has been treated to inactivate viruses.

2. A preparation according to claim 1, wherein the preparation is treated by at least one of chemical or physical measures for viral inactivation.

3. A preparation according to claim 2, wherein the preparation is heat treated for viral inactivation.

4. A preparation according to claim 1, wherein the coagulation protein is a blood factor involved in the intrinsic or extrinsic coagulation pathways.

5. A preparation according to claim 4, wherein the blood factor is an activated coagulation factor or cofactor.

6. A preparation according to claim 5, wherein the activated blood coagulation factor is a vitamin K dependent protein.

7. A preparation according to claim 6, wherein the activated coagulation factor is selected from the group consisting of Factor IIa, Factor VIIa, Factor IXa and Factor Xa.

8. A preparation according to claim 7, wherein said Factor Xa is Factor Xaβ.

9. A preparation according to claim 5, further comprising a protein selected from the group consisting of Factor II, Factor VII, Factor IX, Factor X, protein C, activated protein C, protein S and protein Z.

10. A preparation according to claim 5, further comprising tissue factor.

11. A preparation according to claim 5, further comprising Factor VIII, Factor VIII complex, activated Factor VIII or von Willebrand factor.

12. A preparation according to claim 4, further comprising Factor V or activated factor V.

13. A preparation according to claim 1, wherein said coagulation protein is an enzyme inhibitor or an enzyme.

14. A preparation according to claim 1, wherein said coagulation protein is a coagulation lipoprotein.

15. A preparation according to claim 14, wherein the lipoprotein is Lp(a).

16. A preparation according to claim 1, wherein the preparation is suitable for intravenous administration.

17. A preparation according to claim 1, wherein the phospholipid vesicle have a size of 30 to 900 nm.

18. A preparation according to claim 1, wherein said preparation does not include stabilizers.

19. A preparation according to claim 1, wherein said preparation is frozen or lyophilized.

20. A method for preparing a storage-stable, virus-safe preparation comprising a coagulation protein bound to at least one phospholipid vesicle, comprising:
   (a) contacting a coagulation protein with a phospholipid vesicle dispersion to bind the coagulation protein to at least one phospholipid vesicle by a process selected from the group consisting of
      (i) at least one of co-lyophilization, co-extrusion or sonication of a solution containing the phospholipid vesicle dispersion and the coagulation protein;
      (ii) contacting the phospholipid vesicle dispersion and the coagulation protein with a tenside and then dialyzing to remove the tenside; and
      (iii) mixing the coagulation protein and the phospholipid vesicle dispersion in the presence of charged particles, thereby yielding phospholipid vesicle-bound protein; and
   (b) subjecting the phospholipid vesicle-bound protein to virus inactivation procedures to yield said storage-stable, virus-safe preparation comprising coagulation protein bound to at least one phospholipid vesicle.

21. A method according to claim 20, where said inactivation procedures decrease the biological activity of said coagulation protein by no more than 10%.

22. A method for preparing a storage-stable, virus-safe preparation comprising coagulation protein bound to at least one phospholipid vesicle, comprising:
   (a) hydrating a phospholipid film with a coagulation protein-containing solution to form phospholipid vesicles and binding the coagulation protein to at least one phospholipid vesicle, thereby yielding phospholipid vesicle-bound protein; and
   (b) subjecting the phospholipid vesicle-bound protein to virus inactivation procedures to yield said storage-stable, virus-safe preparation comprising coagulation protein bound to at least one phospholipid vesicle.

23. A method according to claim 22, where said inactivation procedures decrease the biological activity of said coagulation protein by no more than 10%.

24. A method according to claim 22, wherein the phospholipid vesicle-bound protein of step (a) is extruded.

* * * * *